US00PP34487P2

(12) United States Plant Patent
Ammerlaan

(10) Patent No.: US PP34,487 P2
(45) Date of Patent: Aug. 9, 2022

(54) ***ALOE* PLANT NAMED 'OVROCKS09'**

(50) Latin Name: *Aloe aristata*
Varietal Denomination: OVROCKS09

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 17/803,282

(22) Filed: Apr. 19, 2022

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

A new and distinct *Aloe aristata* plant named 'OVROCKS09' which is characterized by succulent foliage that is tightly arranged in a compact basal rosette, dark green foliage that is moderately to densely covered with very light greyed-green protuberances irregularly arranged in transverse rows on the leaf surface, protuberances along the distal centerline of the abaxial foliar surface that are arranged in a distinct line and modified into spines like those of the foliar margins, and finely dentate margins with very light greyed-green teeth. The new variety has shown to be uniform and stable in the resulting generations from asexual propagation.

4 Drawing Sheets

Latin name of the genus and species: The Latin name of the genus and species of the novel variety disclosed herein is *Aloe aristata*.

Variety denomination: The inventive variety of *Aloe* disclosed herein has been given the variety denomination 'OVROCKS09'.

BACKGROUND OF THE INVENTION

Parentage: 'OVROCKS09' is a seedling selection resulting from the controlled pollination of *Aloe aristata* 'Cosmo' (unpatented), the seed parent, with *Aloe aristata* 'Green Pearl' (European Union Community Plant Variety Rights grant number 18402), the pollen parent. The crossing was made by the inventor in the summer of 2019 at a commercial greenhouse in Bleiswijk, the Netherlands. In early 2020, one seedling from said cross was observed to exhibit unique foliage and growth characteristics when compared to the parent plants and all other progenies. After confirming the stability of the unique characteristics first observed, the new plant was selected for commercialization and given the name, 'OVROCKS09'.

Asexual Reproduction: The variety now called 'OVROCKS09' was first asexually propagated by stem cuttings in the fall of 2020 at a greenhouse in Bleiswijk, The Netherlands and has since been vegetatively propagated through five additional generations. Through subsequent generations, the unique features of this cultivar are stable and reproduced true to type.

SUMMARY OF THE INVENTION

The cultivar 'OVROCKS09' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVROCKS09'. These characteristics in combination distinguish 'OVROCKS09' as a new and distinct *Aloe aristata* cultivar:

1. 'OVROCKS09' exhibits an abundance of succulent foliage that is tightly held in a compact basal rosette with secondary rosettes eventually developing at the base of the primary rosette; and
2. 'OVROCKS09' exhibits narrow-ovate to lanceolate foliage with a very upright attitude and a long-apiculate apex with a soft mucronate tip that is curled upward; and
3. 'OVROCKS09' exhibits relatively dark green foliage that is moderately to densely covered with very light greyed-green protuberances that are arranged in irregular transverse rows across the lamina; and
4. 'OVROCKS09' exhibits a subset of protuberances along the distal centerline of the abaxial foliar surface, arranged in an irregular yet distinct longitudinal row, which are modified into spines; and
5. 'OVROCKS09' exhibits finely dentate margins with very light greyed-green teeth.

BOTANICAL DESCRIPTION OF THE PLANT

Figure 1:
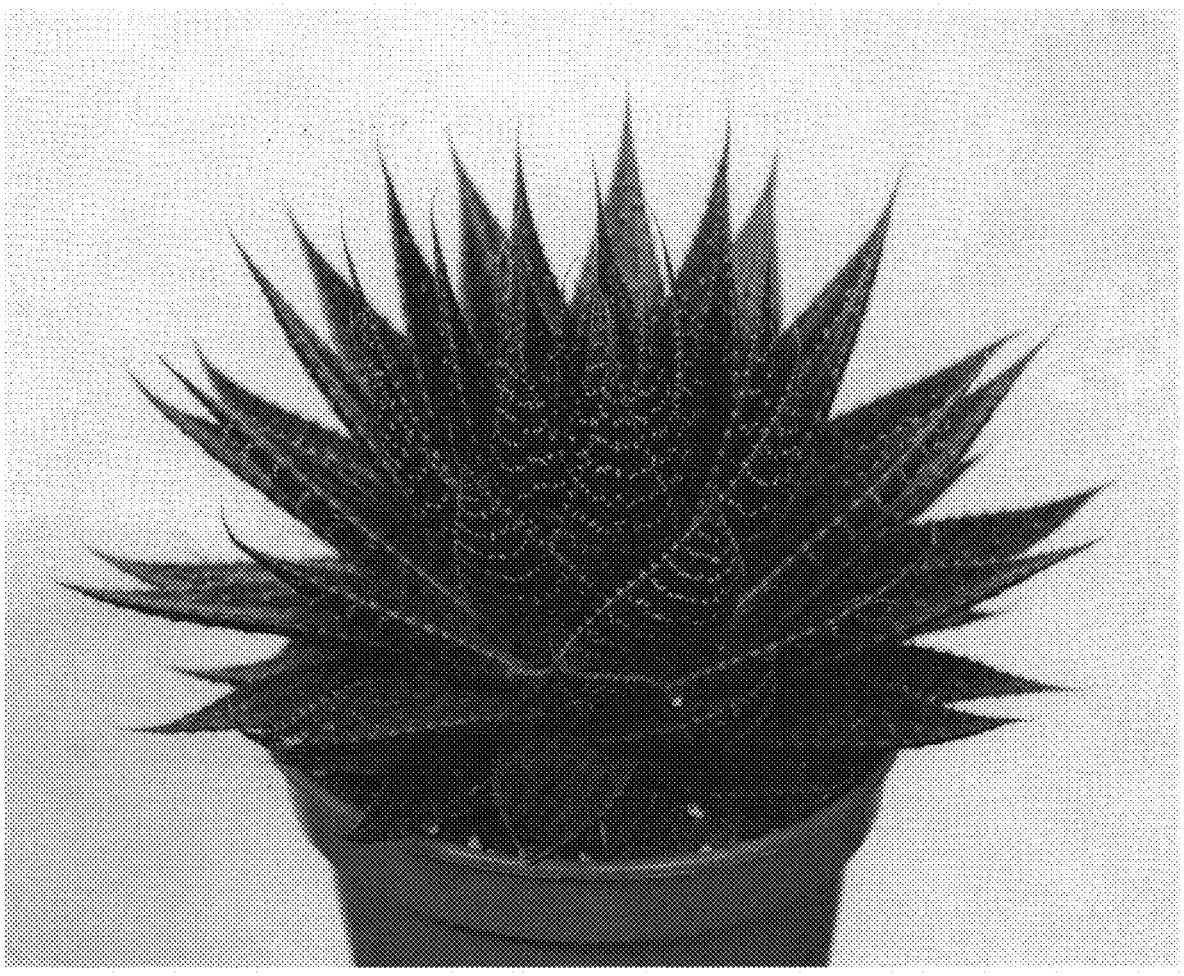
FIG. 1 illustrates, as nearly true as it is reasonably possible to make the same in color photographs of this type, an exemplary plant of 'OVROCKS09' grown in a commercial greenhouse in Bleiswijk, the Netherlands. This plant is approximately 2-year-old, shown planted in a 15 cm container.
Figure 2:
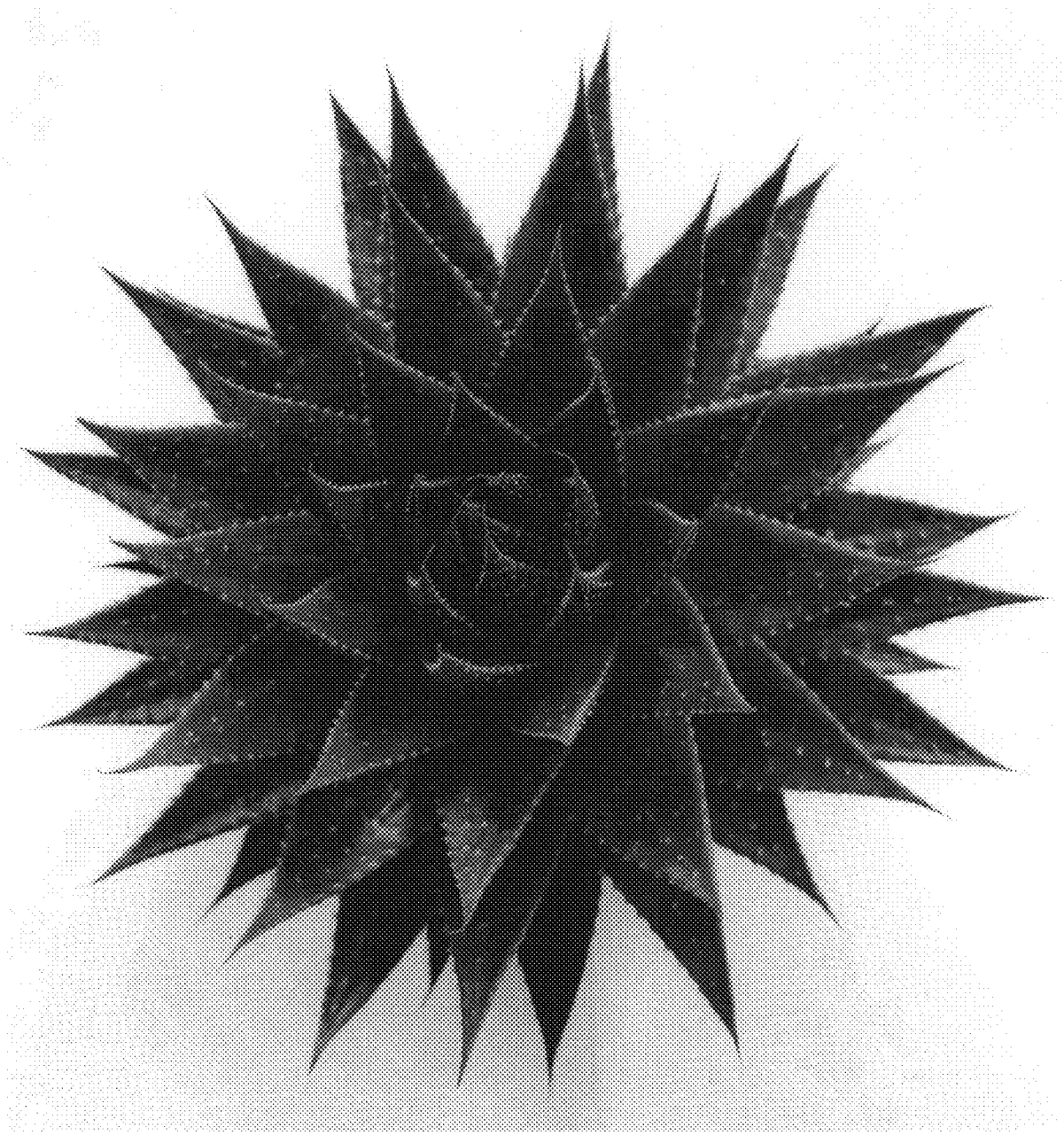
FIG. 2 illustrates, as nearly true as it is reasonably possible to make the same in color photographs of this type, the typical foliage arrangement of 'OVROCKS09'.
Figure 3:
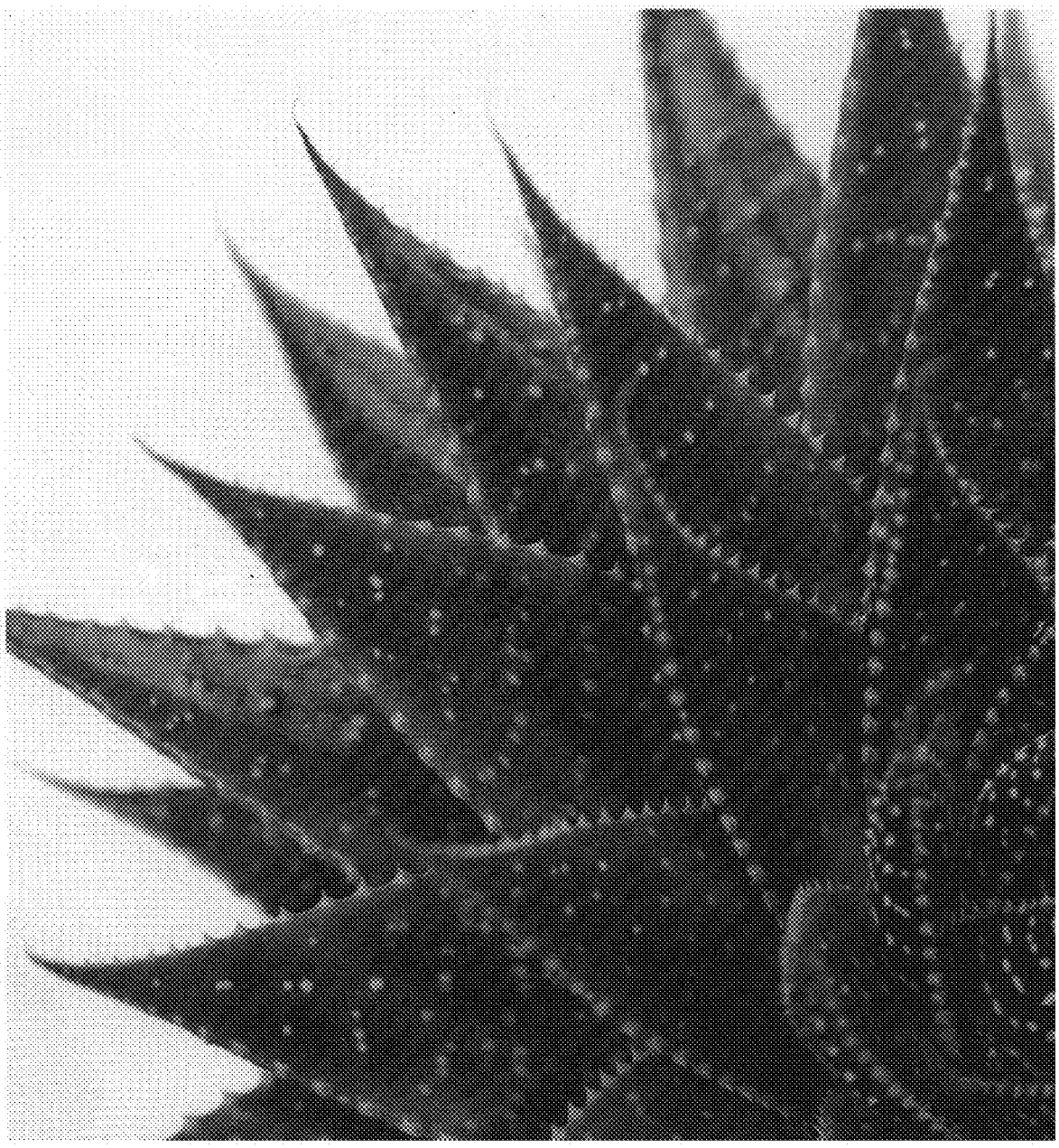
FIG. 3 illustrates, as nearly true as it is reasonably possible to make the same in color photographs of this type, the adaxial surface of the mature foliage 'OVROCKS09'.
Figure 4:
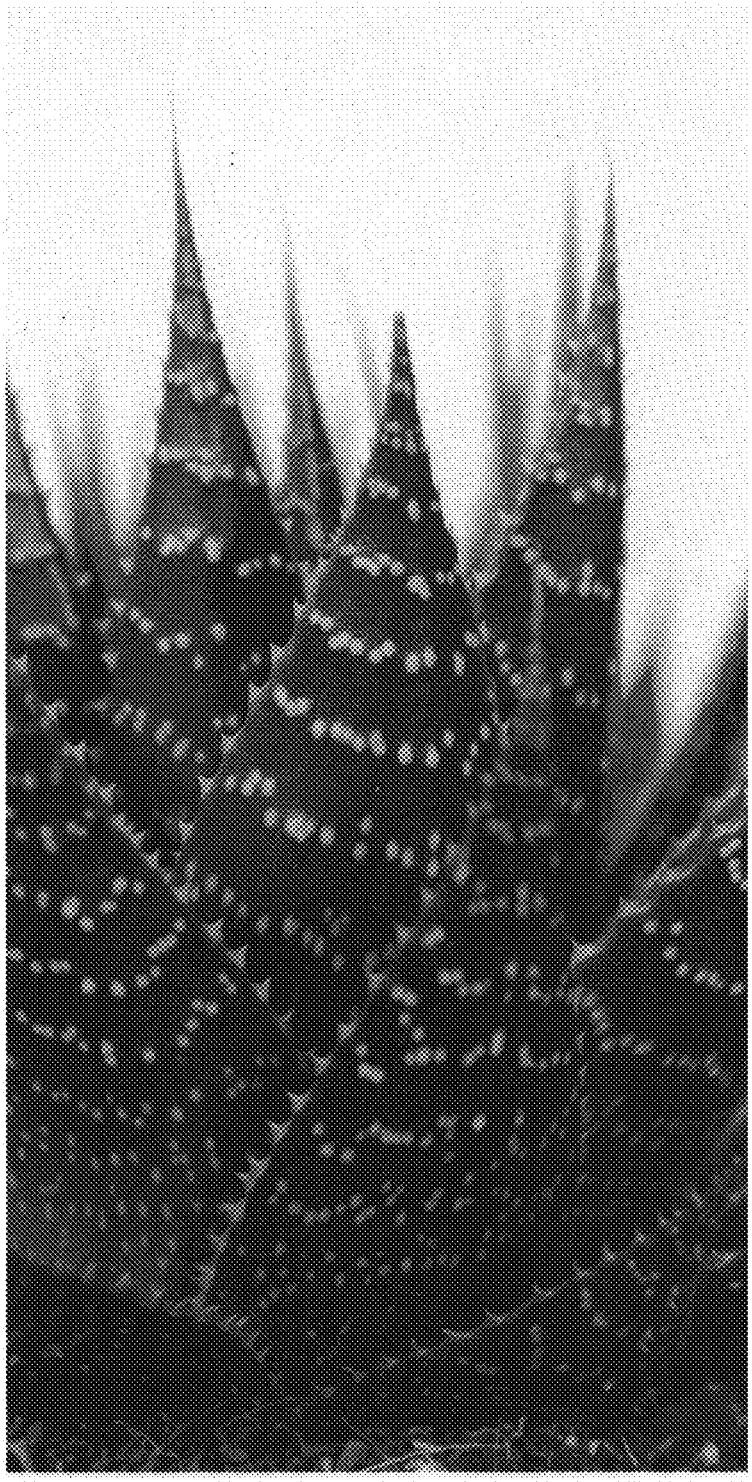
FIG. 4 illustrates, as nearly true as it is reasonably possible to make the same in color photographs of this type, the abaxial surface of the mature foliage 'OVROCKS09'.

The following observations and measurements made in December of 2021 describe averages from a sample set of six specimens of 2-year-old 'OVROCKS09' plants grown in 15 cm nursery containers at commercial greenhouse in Bleiswijk, the Netherlands. Plants were produced using conventional greenhouse production protocols for *Aloe* which consisted of minimal overhead irrigation and fertilizer applications. No pest or disease control measures were utilized in production. Plants were grown under shade (approximately 10,000 lux) and no photoperiodic treatments or artificial light was given to the plants.

Those skilled in the art will appreciate that certain characteristics will vary with older or, conversely, with younger plants. 'OVROCKS09' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVROCKS09' and a comparison with the parent plants and closest known comparator are provided below.

Plant description:

*Growth habit*.—Succulent perennial with foliage that is tightly arranged in a compact basal rosette; as plants age, secondary rosettes eventually develop at the base of the primary rosette.

*Plant form*.—Flattened globular to globular.

*Height from soil level to top of foliar plane*.—13.4 cm.

*Plant spread*.—Average of 12.7 cm.

*Growth rate*.—Moderate rate of growth.

*Plant vigor*.—Moderately to highly vigorous.

*Propagation*.—Type — Leaf cuttings. Time to initiate rooting — Approximately 5 weeks at an approximate temperature of 21 degrees Celsius. Crop time — Approximately 1 year to produce a marketable plant in a 9 cm container.

*Disease and pest resistance or susceptibility*.—Neither resistance nor susceptibility to typical *Aloe aristata* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—No stems or branches; leaves arranged in a basal rosette.

Foliage:

*Arrangement*.—Spirally arranged in a basal rosette.

*Division*.—Simple.

*Attachment*.—Sessile.

*Quantity*.—Approximately 70 leaves per rosette.

*Shape*.—Narrowly ovate to lanceolate.

*Dimensions*.—12.3 cm long, 3.6 cm wide, and 0.95 cm thick.

*Aspect*.—Flat to very slightly concave.

*Attitude*.—Juvenile foliage at and near the center of the rosette exhibits a very upright attitude with an average angle of 75 degrees to horizontal; foliage becomes somewhat more relaxed with age, towards the outer whorls of foliage, at an average angle of 30 degrees from horizontal. The apices of juvenile foliage are curled upward at an average angle of 65 degrees, relative to the lamina.

*Apex*.—Long-apiculate with a soft mucronate tip.

*Base*.—Broad cuneate.

*Margin*.—Finely dentate; teeth have an average length of 0.2 cm and are colored greyed-green, nearest to a mixture of RHS 190C and 190D. Margins are not undulated or lobed.

*Pubescence and texture of the adaxial surface*.—Glabrous, smooth, and moderately covered with small, round protuberances that are arranged in irregular transverse rows across the lamina; protuberances are approximately 0.125 cm in diameter and 0.15 cm tall.

*Pubescence and texture of the abaxial surface*.—Glabrous, smooth, and moderately to densely covered with small, round protuberances that are arranged in irregular transverse rows across the lamina; protuberances are approximately 0.125 cm in diameter and 0.2 cm tall. A small subset of protuberances along the distal centerline are arranged in a distinct line and are modified into spines. These spines are similar in size and color to the dentate teeth along the foliar margins.

*Luster of the adaxial surface*.—Moderately glossy.

*Luster of the abaxial surface*.—Moderately glossy.

*Color*.—Juvenile foliage, adaxial surface — Green, nearest to RHS NN137A, and fading to yellow-green towards the base, nearest to a mixture of RHS 144B, 144C, and 144D. Protuberances are colored greyed-green, nearest to a mixture of RHS 191C and 191D. Juvenile foliage, abaxial surface — Green, nearest to a mixture of RHS NN137A and NN137B, and fading to yellow-green towards the base, nearest to RHS 145A. Protuberances are colored greyed-green, nearest to RHS 191D. Mature foliage, adaxial surface — Green, nearest to RHS NN137A, and fading to yellow-green towards the base, nearest to a mixture of RHS 147C and 147D. Protuberances are colored greyed-green, nearest to RHS 191C. Mature foliage, abaxial surface — Nearest to in between green and yellow-green, RHS NN137B and 147A; fading to yellow-green towards the base, nearest to a mixture of RHS 147B, 147C, and 147D. Protuberances are colored greyed-green, nearest to RHS 191D.

*Venation*.—Pattern — No venation is visible. Color, adaxial surface — No venation is visible. Color, abaxial surface — No venation is visible.

*Petiole*.—No petiole; leaves are sessile.

Inflorescence: No flowering has been observed to date.

COMPARISONS WITH THE PARENT PLANTS

Plants of the new cultivar 'OVROCKS09' differ from the seed parent, *Aloe aristata* 'Cosmo' (not patented), in the following characteristics described in Table 1 below.

TABLE 1

| Characteristic | 'OVROCKS09' | 'Cosmo' |
|---|---|---|
| Abundance of foliage. | Less abundant than 'Cosmo'. | More abundant than 'OVROCKS09'. |
| Foliage size. | Larger than 'Cosmo'. | Smaller than 'OVROCKS09'. |
| General coloration of the mature, adaxial foliar surface; at and near the base. | Generally appearing as darker shade of yellow-green, relative to 'Cosmo'. | Generally appearing as a lighter shade of yellow-green, relative to 'OVROCKS09'. |
| General coloration of the mature, adaxial foliar surface; excluding the base. | Generally appearing as lighter shade of green, relative to 'Cosmo'. | Generally appearing as a darker shade of green, relative to 'OVROCKS09'. |

Plants of the new cultivar 'OVROCKS09' differ from the seed parent, *Aloe aristata* 'Green Pearl' (European Union Community Plant Variety Rights grant number 18402), in the following characteristics described in Table 2 below.

TABLE 2

| Characteristic | 'OVROCKS09' | 'Green Pearl' |
|---|---|---|
| Abundance of foliage. | Less abundant than 'Green Pearl'. | More abundant than 'OVROCKS09'. |

TABLE 2-continued

| Characteristic | 'OVROCKS09' | 'Green Pearl' |
|---|---|---|
| Foliage shape. | Narrower than the parent. | Broader than 'OVROCKS09'. |
| Foliar apex. | Mucronate tip is longer than that of 'Green Pearl'. | Mucronate tip is shorter than that of 'OVROCKS09'. |
| Luster of the foliage. | Moderately glossy. | Highly glossy. |

COMPARISON WITH THE CLOSEST KNOWN COMPARATOR

Plants of the new cultivar 'OVROCKS09' differ from the most similar variety known to the inventor, *Aloe aristata* 'AMIAL1605' (U.S. Plant Pat. No. 28,982), in the following characteristics described in Table 3 below.

TABLE 3

| Characteristic | 'OVROCKS09' | 'AMIAL1605' |
|---|---|---|
| Plant size. | Larger than 'AMIAL1605'. | Smaller than 'OVROCKS09'. |
| Abundance of foliage. | Less abundant than 'AMIAL1605. | More abundant than 'OVROCKS09'. |
| Foliage shape. | Narrowly ovate to lanceolate with a long apiculate apex, and a long, soft mucronate tip. | Ovate foliage with an acute to broadly acute apex, and a short caudate tip. |
| General coloration of the foliage. | Generally appearing as lighter green by comparison to 'AMIAL1605'. | Generally appearing as darker green by comparison to 'OVROCKS09'. |

That which is claimed is:

1. A new and distinct variety of *Aloe aristata* plant named 'OVROCKS09', substantially as described and illustrated herein.

* * * * *